US010544384B2

(12) United States Patent
Scheuermann et al.

(10) Patent No.: US 10,544,384 B2
(45) Date of Patent: Jan. 28, 2020

(54) SKIN CLEANSING COMPOSITION CONTAINING RHAMNOLIPID AND SILOXANE

(71) Applicant: Evonik Degussa GmbH, Essen (DE)

(72) Inventors: Ralph Scheuermann, Bottrop (DE); Marcel Pickl, Bottrop (DE); Michael Ferenz, Essen (DE); Hans Henning Wenk, Mülheim an der Ruhr (DE); Martin Schilling, Bonn (DE); Kathrin Daniela Brandt, Düsseldorf (DE); Verena Dahl, Kürten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/546,297

(22) PCT Filed: Feb. 8, 2016

(86) PCT No.: PCT/EP2016/052586
§ 371 (c)(1),
(2) Date: Jul. 26, 2017

(87) PCT Pub. No.: WO2016/134958
PCT Pub. Date: Sep. 1, 2016

(65) Prior Publication Data
US 2018/0016525 A1 Jan. 18, 2018

(30) Foreign Application Priority Data
Feb. 27, 2015 (EP) .................... 15156961

(51) Int. Cl.
C11D 9/36 (2006.01)
C11D 3/37 (2006.01)
A61K 8/60 (2006.01)
A61Q 19/10 (2006.01)
A61K 8/894 (2006.01)
C11D 1/06 (2006.01)
C11D 1/83 (2006.01)
C11D 1/82 (2006.01)

(52) U.S. Cl.
CPC .......... C11D 3/3738 (2013.01); A61K 8/602 (2013.01); A61K 8/894 (2013.01); A61Q 19/10 (2013.01); C11D 1/06 (2013.01); C11D 1/83 (2013.01); A61K 2800/86 (2013.01); C11D 1/82 (2013.01)

(58) Field of Classification Search
CPC ........ C11D 3/0094; C11D 3/162; C11D 3/22; C11D 3/373; C11D 3/3738; C11D 9/36
See application file for complete search history.

(56) References Cited

U.S. PATENT DOCUMENTS 7,157,541 B2 1/2007 Knott et al.
7,442,666 B2 10/2008 Herrwerth et al.
7,598,334 B2 10/2009 Ferenz et al.
7,605,284 B2 10/2009 Brueckner et al.
7,635,581 B2 12/2009 Ferenz et al.
7,727,599 B2 6/2010 Doehler et al.
7,776,989 B2 8/2010 Ferenz et al.
7,825,207 B2 11/2010 Ferenz et al.
7,834,122 B2 11/2010 Ferenz et al.
7,855,265 B2 12/2010 Thum et al.
7,964,694 B2 6/2011 Ferenz et al.
7,985,722 B2* 7/2011 DeSanto ............... A01N 43/16
                                                    510/160
7,994,110 B2 8/2011 Wenk et al.
8,138,294 B2 3/2012 Henning et al.
8,198,473 B2 6/2012 Ferenz et al.
8,211,972 B2* 7/2012 Meyer ................. A61K 8/0208
                                                    524/588
8,420,748 B2 4/2013 Henning et al.
8,455,603 B2 6/2013 Ferenz et al.
8,466,248 B2 6/2013 Meyer et al.
8,557,944 B2 10/2013 Henning et al.
8,617,529 B2 12/2013 Herrwerth et al.
8,685,376 B2 4/2014 Czech et al.
8,729,207 B2 5/2014 Hartung et al.
8,778,319 B2 7/2014 Herrwerth et al.
8,802,744 B2 8/2014 Knott et al.
8,841,400 B2 9/2014 Henning et al.
(Continued)

FOREIGN PATENT DOCUMENTS

DE 102008001788 A1 11/2009
EP 1520870 A1 4/2005
(Continued)

OTHER PUBLICATIONS

European Search Report dated Aug. 26, 2015 in EP 15 15 6961 (6 pages).
"Emollient Cleansing Bath," Mintel, Copyright Oct. 2008 (3 pages).
Brandt et al., U.S. Appl. No. 15/380,001, filed Dec. 15, 2016.
German language International Search Report dated Apr. 19, 2016 in PCT/EP2016/052586 (4 pages).
German language Written Opinion dated Apr. 19, 2016 in PCT/EP2016/052586 (6 pages).
(Continued)

Primary Examiner — Charles I Boyer
(74) Attorney, Agent, or Firm — Philip P. McCann; Nexsen Pruet PLLC

(57) ABSTRACT

The invention provides compositions comprising at least one rhamnolipid and at least one siloxane, characterized in that the weight ratio of rhamnolipid to siloxane is from 5,000,000:1 to 100:1, preferably from 500,000:1 to 1000:1, particularly preferably from 25,000:1 to 2500:1. In another embodiment, the invention provides compositions include rhamnolipid in an amount of from 0.5% by weight to 70% by weight, preferably from 2% by weight to 60% by weight, particularly preferably from 3% by weight to 50% by weight, where the percentages by weight refer to the total composition.

20 Claims, No Drawings

(56) References Cited

U.S. PATENT DOCUMENTS

| | | | |
|---|---|---|---|
| 8,916,511 B2 | 12/2014 | Maurer et al. | |
| 8,946,369 B2 | 2/2015 | Henning et al. | |
| 8,957,009 B2 | 2/2015 | Schubert et al. | |
| 9,005,928 B2 | 4/2015 | Schaffer et al. | |
| 9,138,385 B2 | 9/2015 | Dahl et al. | |
| 9,243,212 B2 | 1/2016 | Kuppert et al. | |
| 9,271,908 B2 | 3/2016 | Allef et al. | |
| 9,353,225 B2 | 5/2016 | Knott et al. | |
| 9,434,755 B2 | 9/2016 | Schilling et al. | |
| 9,580,720 B2 | 2/2017 | Schaffer et al. | |
| 2006/0155090 A1 | 7/2006 | Ferenz et al. | |
| 2006/0275238 A1 | 12/2006 | Blasko-Begoihn et al. | |
| 2007/0197678 A1 | 8/2007 | Cavaleiro et al. | |
| 2010/0034765 A1 | 2/2010 | Herrwerth et al. | |
| 2010/0248325 A1 | 9/2010 | Eckstein et al. | |
| 2011/0206623 A1 | 8/2011 | Wenk et al. | |
| 2013/0040869 A1* | 2/2013 | Cox | A61K 8/44 510/119 |
| 2013/0259821 A1 | 10/2013 | Henning et al. | |
| 2013/0331952 A1 | 12/2013 | Halldorsson et al. | |
| 2014/0296125 A1* | 10/2014 | Kuppert | C11D 1/74 510/356 |
| 2014/0296168 A1 | 10/2014 | Schilling et al. | |
| 2016/0075846 A1 | 3/2016 | Krebs et al. | |
| 2016/0081890 A1* | 3/2016 | Stevenson | A61Q 5/02 424/401 |
| 2016/0160009 A1 | 6/2016 | Ferenz et al. | |
| 2016/0161001 A1 | 6/2016 | Klotzbach et al. | |
| 2016/0272667 A1* | 9/2016 | Lohitharn | C07H 15/04 |
| 2016/0311963 A1 | 10/2016 | Lobert et al. | |
| 2016/0319094 A1 | 11/2016 | Diendort et al. | |
| 2017/0202770 A1 | 7/2017 | Friedrich et al. | |

FOREIGN PATENT DOCUMENTS

| | | |
|---|---|---|
| EP | 1627892 A1 | 2/2006 |
| EP | 2786742 A1 | 10/2014 |
| EP | 2786743 A1 | 10/2014 |
| EP | 2787065 A1 | 10/2014 |
| WO | 2008013899 A2 | 1/2008 |
| WO | 2012013554 A1 | 2/2012 |

OTHER PUBLICATIONS

International Search Report dated Apr. 19, 2016 in PCT/EP2016/052586 (3 pages).
Lobert et al., U.S. Appli. No. 15/508,386, filed Mar. 2, 2017.
Lobert et al., U.S. Appl. No. 15/540,605, filed Jun. 29, 2017.
Peggau et al., U.S. Appl. No. 15/509,685, filed Mar. 8, 2017.
Schilling et al., U.S. Appl. No. 15/520,157, filed Apr. 19, 2017.

* cited by examiner

SKIN CLEANSING COMPOSITION CONTAINING RHAMNOLIPID AND SILOXANE

This application is a national stage application under 35 U.S.C. § 371 of International Application No. PCT/EP2016/052586 filed 8 Feb. 2016, which claims priority to EP Application No. 15156961.3 filed 27 Feb. 2015, the disclosures of which are expressly incorporated herein by reference.

FIELD

The invention provides compositions comprising at least one rhamnolipid and at least one siloxane, characterized in that the weight ratio of rhamnolipid to siloxane is from 5,000,000:1 to 100:1, preferably from 500,000:1 to 1000:1, particularly preferably from 25,000:1 to 2500:1.

BACKGROUND

Rhamnolipids for use in cosmetics or as cleaners have been known for a long time.

Thus, for example, EP2786742 describes cosmetic formulations comprising at least one rhamnolipid.

EP2786743 discloses mixture compositions comprising rhamnolipids and their use for producing cosmetic formulations or cleaning formulations.

EP2787065 discloses detergent formulations for textiles comprising rhamnolipids with a majority content of di-rhamnolipids.

SUMMARY

It was an object of the invention to provide compositions which lead to an improved removal of undesired odors on the skin.

Surprisingly, it has been found that compositions comprising rhamnolipids are able to achieve the object set for the invention if only small amounts of siloxane are present.

DETAILED DESCRIPTION

The present invention therefore provides compositions comprising at least one rhamnolipid and at least one siloxane, characterized in that the weight ratio of rhamnolipid to siloxane is from 5,000,000:1 to 100:1, preferably from 500,000:1 to 1000:1, particularly preferably from 25,000:1 to 2500:1.

The invention further provides formulations comprising the compositions according to the invention.

It is a further advantage of the present invention that the compositions according to the invention can have an outstanding cleaning performance coupled with the retention of the structure of suede.

Another advantage of the present invention is that the compositions according to the invention can eliminate undesired odors from skin and at the same time leave behind a good skin feel. Another advantage of the present invention is that the compositions according to the invention can give rise to a large amount of foam in surface-active formulations.

A further advantage of the present invention is that the compositions according to the invention are able to give rise to a readily spreadable foam, in particular on skin and hair, in surface-active formulations. They are suitable e.g. for producing shaving foams with improved consistency and spreadability on the skin.

A further advantage of the present invention is that the foams have a relatively fine pore structure and a relatively high water content and as a result have better haptics.

A further advantage of the present invention is that the compositions according to the invention can bring about increased shine on hard surfaces such as, for example, plastic and glass for a simultaneously exceptional cleaning performance.

A further advantage of the present invention is that the compositions according to the invention can have an outstanding cleaning performance coupled with a good rewettability of textiles.

The term "rhamnolipid" in the context of the present invention is understood to mean particularly compounds of the general formula (I) or salts thereof,

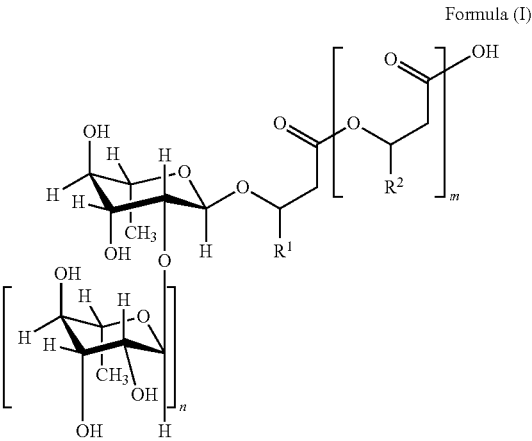

Formula (I)

where
m=2, 1 or 0, in particular 1,
n=1 or 0,
$R^1$ and $R^2$=mutually independently, identical or different, organic radical having 2 to 24, preferably 5 to 13 carbon atoms, in particular optionally branched, optionally substituted, particularly hydroxy-substituted, optionally unsaturated, in particular optionally mono-, bi- or tri-unsaturated alkyl radical, preferably those selected from the group consisting of pentenyl, heptenyl, nonenyl, undecenyl and tridecenyl and $(CH_2)_o$—$CH_3$ where o=1 to 23, preferably 4 to 12.

The term "di-rhamnolipid" in the context of the present invention is understood to mean compounds of the general formula (I) or salts thereof, where n=1.

The term "mono-rhamnolipid" in the context of the present invention is understood to mean compounds of the general formula (I) or salts thereof, where n=0.

Distinct rhamnolipids are abbreviated according to the following nomenclature: "diRL-CXCY" is understood to mean di-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

"monoRL-CXCY" is understood to mean mono-rhamnolipids of the general formula (I), in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used therefore does not distinguish between "CXCY" and "CYCX". For rhamnolipids where m=0, monoRL-CX or diRL-CX is used accordingly.

If one of the abovementioned indices X and/or Y is provided with ":Z", this signifies that the respective radical $R^1$ and/or $R^2$ is equal to an unbranched, unsubstituted hydrocarbon radical having X-3 or Y-3 carbon atoms having Z double bonds.

To determine the content of rhamnolipids in the context of the present invention, only the mass of the rhamnolipid anion is considered, i.e. "general formula (I) less one hydrogen".

To determine the content of rhamnolipids in the context of the present invention, all rhamnolipids are converted by acidification into the protonated form (cf. general formula (I)) and quantified by HPLC.

The content of siloxane can be determined for example using a suitable internal standard, preferably the identical siloxane, by means of $^1$H-NMR (nuclear magnetic resonance spectroscopy), optionally with prior extractive or chromatographic enrichment for increasing the detection limit.

The weight ratio of rhamnolipid to siloxane in the compositions according to the invention refers to the sum of all rhamnolipids present in the compositions according to the invention to the sum of all siloxanes present in the compositions according to the invention.

The weight ratio of rhamnolipid to siloxane in the formulations according to the invention refers to the sum of all rhamnolipids present in the formulations according to the invention to the sum of all siloxanes present in the formulations according to the invention.

Unless otherwise stated, all percentages (%) given are percentages by weight.

The term ppm (=parts per million) likewise describes weight fractions.

The term "aqueous" in connection with the present invention is understood to mean a composition which comprises at least 5% by weight of water, based on the total compositions under consideration.

The "pH" in connection with the present invention is defined as the value which is measured for the relevant substance at 25° C. after stirring for 5 minutes using a pH electrode calibrated in accordance with ISO 4319 (1977).

The rhamnolipids present in the compositions according to the invention are present at least partially as salt on account of the given pH.

In compositions preferred according to the invention the cations of the rhamnolipid salts present are selected from the group comprising, preferably consisting of, $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions.

Exemplary representatives of suitable ammonium ions are tetramethylammonium, tetraethylammonium, tetrapropylammonium, tetrabutylammonium and [(2-hydroxyethyl)trimethylammonium] (choline) and also the cations of 2-aminoethanol (ethanolamine, MEA), diethanolamine (DEA), 2,2',2"-nitrilotriethanol (triethanolamine, TEA), 1-aminopropan-2-ol (monoisopropanolamine), ethylenediamine, diethylenetriamine, triethylenetetramine, tetraethylenepentamine, 1,4-diethylenediamine (piperazine), aminoethylpiperazine and aminoethylethanolamine.

Mixtures of the abovementioned cations may also be present as cations of the rhamnolipid salts present according to the invention.

Particularly preferred cations are selected from the group comprising, preferably consisting of, $Na^+$, $K^+$, $NH_4^+$ and the triethanolammonium cation.

The total amount of the abovementioned cations preferably accounts for 70% by weight to 99% by weight, particularly preferably 80% by weight to 90% by weight, of all cations present in the composition except $H^+$ and $H_3O^+$.

Preferred compositions according to the invention comprise 50% by weight to 99% by weight, preferably 70% by weight to 95% by weight, particularly preferably 85% by weight to 90% by weight, of rhamnolipid anions, where % by weight refers to all anions present in the composition except $OH^-$.

Preference is given to compositions according to the invention which are characterized in that they comprise the rhamnolipid in an amount of from 0.5% by weight to 70% by weight, preferably from 2% by weight to 60% by weight, particularly preferably from 3% by weight to 50% by weight, where the percentages by weight refer to the total composition and take all rhamnolipids present in the composition into consideration.

In particular, preferred compositions according to the invention are characterized in that they comprise the rhamnolipid in an amount of from 3% by weight to 50% by weight and in that the weight ratio of rhamnolipid to siloxane is from 25,000:1 to 1000:1.

In a preferred embodiment of the compositions according to the invention, they are concentrates which comprise the rhamnolipid in an amount of from 12% by weight to 70% by weight, preferably from 15% by weight to 60% by weight, particularly preferably from 20% by weight to 50% by weight, where the percentages by weight refer to the total composition and take all rhamnolipids present in the composition into consideration. These concentrates preferably have a viscosity of 0.2 Pas to 10 Pas, preferably from 1.2 Pas to 5 Pas, particularly preferably from 1.5 Pas to 3 Pas, measured in a rheometer at 25° C. and at a shear rate of 10 $s^{-1}$. The concentrates according to the invention are preferably characterized in that they comprise the rhamnolipid in an amount of from 20% by weight to 50% by weight and in that the weight ratio of rhamnolipid to siloxane is from 25,000:1 to 1000:1.

In an alternative preferred embodiment of the compositions according to the invention, they are ready-to-use formulations which comprise the rhamnolipid in an amount of from 0.5% by weight to 10% by weight, preferably from 2.5% by weight to 8% by weight, particularly preferably from 3% by weight to 7% by weight, where the percentages by weight refer to the total composition and take all rhamnolipids present in the composition into consideration. The ready-to-use formulations according to the invention are preferably characterized in that they comprise the rhamnolipid in an amount of from 3% by weight to 7% by weight and in that the weight ratio of rhamnolipid to siloxane is from 25,000:1 to 1000:1.

A composition preferred according to the invention is characterized in that it comprises a mixture of rhamnolipids, where the weight ratio of di-rhamnolipids to mono-rhamnolipids in the mixture is greater than 51:49, preferably greater than 75:25, particularly preferably 97:3, particularly greater than 98:2.

A composition preferred according to the invention is characterized in that the rhamnolipid mixture comprises 51% by weight to 95% by weight, preferably 70% by weight to 90% by weight, particularly preferably 75% by weight to 85% by weight, of diRL-C10C10 and 0.5% by weight to 9% by weight, preferably 0.5% by weight to 3% by weight, particularly preferably 0.5% by weight to 2% by weight, of monoRL-C10C10, where the percentages by weight refer to the sum total of all rhamnolipids present.

A composition preferred according to the invention is characterized in that the rhamnolipid mixture, in addition to the diRL-C10C10 and monoRL-C10C10 contents mentioned above, comprises 0.5% by weight to 15% by weight, preferably 3% by weight to 12% by weight, particularly preferably 5% by weight to 10% by weight, of diRL-C10C12:1, where the percentages by weight refer to the sum total of all rhamnolipids present.

A composition preferred according to the invention is characterized in that the rhamnolipid mixture, in addition to the diRL-C10C10 and monoRL-C10C10 contents mentioned above, comprises 0.1% by weight to 5% by weight, preferably 0.5% by weight to 3% by weight, particularly preferably 0.5% by weight to 2% by weight, of monoRL-C10C12 and/or, preferably and 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

It can be advantageous and is therefore preferred if the rhamnolipid mixture present in the composition according to the invention, in addition to the diRL-C10C10 and monoRL-C10C10 contents mentioned above, comprises 0.1% by weight to 25% by weight, preferably 2% by weight to 10% by weight, particularly preferably 4% by weight to 8% by weight, of diRL-C8C10, where the percentages by weight refer to the sum total of all rhamnolipids present.

A composition particularly preferred according to the invention is characterized in that the rhamnolipid mixture, in addition to the diRL-C10C10 and monoRL-C10C10 contents mentioned above, comprises 0.5% by weight to 15% by weight, preferably 3% by weight to 12% by weight, particularly preferably 5% by weight to 10% by weight, of diRL-C10C12:1, 0.5 to 25% by weight, preferably 5% by weight to 15% by weight, particularly preferably 7% by weight to 12% by weight, of diRL-C10C12, 0.1% by weight to 5% by weight, preferably 0.5% by weight to 3% by weight, particularly preferably 0.5% by weight to 2% by weight, of monoRL-C10C12 and 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

It is moreover preferred if the rhamnolipid mixture present in the composition according to the invention comprises only small amounts of rhamnolipids of the formula monoRL-CX or diRL-CX. In particular, the mixture composition according to the invention preferably comprises 0% by weight to 5% by weight, preferably 0.001% by weight to 3% by weight, particularly preferably 0.01% by weight to 1% by weight, of diRLC10, where the percentages by weight refer to the sum total of all rhamnolipids present, and the term "0% by weight" is understood to mean no detectable amount.

The compositions according to the invention are particularly preferably aqueous compositions.

The compositions according to the invention preferably have a pH of 5.5 to 6.9, preferably of 5.6 to 6.2, particularly preferably of 5.6 to 6.0.

Methods for preparing the corresponding rhamnolipid mixtures are disclosed, for example, in EP2786743 and EP2787065.

The siloxanes present in the compositions according to the invention are compounds with Si—O—Si bonds. In them, silicon atoms are not bonded to one another directly, but via oxygen atoms. The properties and the synthesis of siloxanes is described in "Walter Noll, Chemie and Technologie der Silicone, Verlag Chemie GmbH, 2nd edition, 1968", "S. J. Clarson, J. A. Semlyen, Siloxane Polymers, PTR Prentice Hall, ISBN 0-13-816315-4" or also in "Silicones, Vulkan-Verlag Essen ISBN: 3-8027-2161-6" and in "Moretto, H.-H., Schulze, M. and Wagner, G. 2000. Silicones. Ullmann's Encyclopedia of Industrial Chemistry".

A distinction is often made between organomodified siloxanes and so-called silicone oils.

Silicone oils are polymers with siloxane units which carry only methyl or phenyl groups as organic radicals. Silicone oils are used in a multitude of technical processes.

Simple linearly polymeric silicone oils are composed of units $(R_2SiO)x$ and can be described by the following general formula:

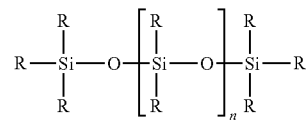

R=Me or Ph,

In accordance with the systematics of organic polymers, the following groups can be differentiated according to Noll:
(a) linear polysiloxanes (see above)
(b) branched polysiloxanes: These comprise trifunctional or tetrafunctional siloxane units as branching building blocks. The branching point is either incorporated into a chain or a ring.
(c) Cycl. polysiloxanes: These are composed as rings from difunctional siloxane units.
(d) Crosslinked polymers: In this group, chain-like or ring-like molecules are linked with the help of T units and Q units to give two-dimensional or three-dimensional networks.

Within each polymer group, a further division can be performed depending on the type of substituents bonded to the silicon atom. The siloxane backbone can be laden with different types of hydrocarbon radials; it can furthermore comprise silicon-functional or organofunctional groups or both at the same time. Accordingly, subdivision of the polymer groups into non-functional and into silicon-functional or organofunctional polysiloxanes is expedient.

The siloxanes can be of low viscosity to high viscosity or solid depending on chain length, degree of branching and substituents.

If the radical R in

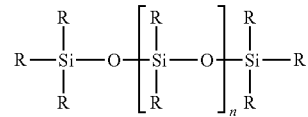

is an alkyl group with two or more carbon atoms, the term silicone waxes is also used. These can be prepared for example by the hydrosilylation of olefins with SiH-functional siloxanes, as is shown in the literature listed above. Silicone waxes are used for example in personal care formulations. Typical alkyl radicals are octyl, dodecyl or hexadecyl.

A further class of siloxanes are the polydiethylsiloxanes in which ethyl groups are bonded to the silicon atoms. Typical representatives of this substance class are described with the CAS number 63148-61-8 and are likewise used as lubricant.

Furthermore, there is a large number of siloxanes with fluorinated alkyl radicals which are used, for example, as lubricants.

A further class of suitable siloxanes is siloxanes having functional groups, such as, for example, amino functions. Siloxanes of this type are described inter alia with the CAS number 99363-37-8 or the CAS number 7150-79-3. The two substance classes are used in shampoos or conditioners for hair.

A large number of further functional groups may be bonded to a siloxane backbone. Moreover, mixtures of different functionalities can be bonded to a polymer backbone. Different ways for this are described in the literature listed above. To be emphasized in this connection is hydrosilylation, in which SiH-functional siloxanes are reacted with unsaturated organic compounds.

All of the siloxanes listed above can be used in the siloxanes according to the invention.

Preference is given to using organomodified siloxanes. These are particularly preferably polyethersiloxanes and especially preferably polyethersiloxanes of the general formula II. Polyethersiloxanes are siloxanes which have both siloxane units and polyether units. Siloxane units are units of the general formula —Si($R^{S1}$)$_2$O. Here, $R^{S1}$ is a hydrocarbon radical having 1-20 carbon atoms, preferably $R^{S1}$ is a methyl group.

Particular preference is given to polyethersiloxanes:

Formula II

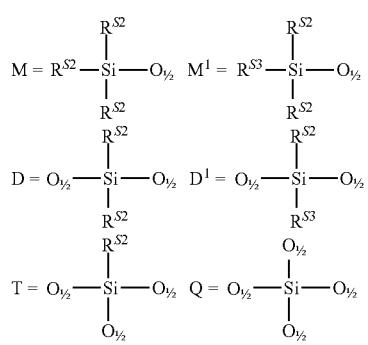

a=0-20, preferably 0-10, in particular 2,
b=0-20, preferably 0-10, in particular 0,
c=3-2000, preferably 5-1000, in particular 10-500,
d=0-50, preferably 1-30, in particular 1.5-15,
e=0-20, preferably 0-10, in particular 0,
f=0-20, preferably 0-10, in particular 0,
here, the limitation applies a+b≥2 and N=a+b+c+d+e+f≤2050, b+d≥1
$R^{S2}$=mutually independently, identical or different, alkyl radicals having 1-16 carbon atoms or aryl radicals having 6-16 carbon atoms or H or —OR$^{S4}$, preferably methyl, ethyl, phenyl, octyl, dodecyl or H, in particular methyl.

Here, $R^{S4}$ is, mutually independently, identical or different alkyl radicals having 1-16 carbon atoms or aryl radicals having 6-16 carbon atoms or H, $R^{S3}$=mutually independently, identical or different, polyether radicals, preferably identical or different polyether radicals of the general formula III

Formula III $R^{S5}$=identical or different alkyl radicals having 1 to 18 carbon atoms which optionally have ether functions, or aryl radicals having 6-18 carbon atoms which optionally have ether functions, or H, preferably H, ethyl and benzyl,
$R^{S6}$=identical or different radicals from the group: $R^{S8}$, H, —C(O)$R^{S8}$, preferably methyl, butyl, H or —C(O)Me,
$R^{S7}$=mutually independently, identical or different, divalent organic radicals, preferably identical or different divalent organic radicals having 2-30 carbon atoms which are optionally interrupted by ether functions and optionally carry OH functions, preferably —(CH$_2$)$_3$—
$R^{S8}$=mutually independently, identical or different, alkyl radicals having 1-16 carbon atoms or aryl radicals having 6-16 carbon atoms,
h=0 or 1,
i=0-200, preferably 0-100, especially preferably 0-50,
j=0-200, preferably 0-100, especially preferably 0-50,
k=0-200, preferably 0-100, especially preferably 0-50,
l=0-80, preferably 0-40, especially preferably 0,
with the proviso i+j+k+l≥3.

To describe the siloxanes, a style analogous to the literature: Walter Noll, Chemie and Technologie der Silicone [Chemistry and technology of silicones], Verlag Chemie GmbH, 2nd edition, 1968, is selected here. The polyethersiloxanes according to the invention have different siloxane units which can be combined with one another in the molecule in different ways. Furthermore, the description of siloxanes with M, D, T and Q units is disclosed in the book Silicones, (Silicones, G. G. Freeman, The Plastic Institute, 1962, page 22-23.).

The composition of the siloxane units arises taking into consideration the fact that each oxygen atom acts as a bridging member between every two silicon atoms, and accordingly only half is to be attributed to each silicon atom. The different siloxane units are bonded with one another via 2 half oxygen atom (—O$_{1/2}$O$_{1/2}$—) groups, as a result of which an oxygen bridge (—O—) is shown. Of particular importance are polyether siloxanes comprising polyether radicals linked to a siloxane backbone via SiC functions. They can be prepared by the hydrosilylation of polyethers with terminal CC double bonds with SiH-siloxanes. C—C double bond-containing polyethers can be prepared, for example, by the alkoxylation of allyl alcohol and are marketed as allyloxypolyethylene glycols. Typical representatives of this substance class are described, for example, using the CAS numbers 27274-31-3, 9042-19-7 and 9041-33-2.

The preparation of polyethersiloxanes by means of hydrosilylation is a known process and is described widely in the literature, for example in the book "Chemie and Technologie der Silicone [Chemistry and technology of silicones]", Verlag Chemie, 1960, page 43. The catalysts typically employed for hydrosilylation are platinum compounds. In commercial practice the use of hexachroplatinic acid and Karstedt's catalyst and/or formulations thereof has become established for this purpose.

The siloxanes present in the compositions according to the invention are preferably present in an amount of from 0.1 ppm to 5000 ppm, preferably from 1 ppm to 4000 ppm, particularly preferably from 10 ppm to 2000 ppm, where the ppm refer to the total composition.

In the preferred "concentrates" embodiment of the compositions according to the invention already specified above, the siloxane is present preferably in an amount of 0.5 ppm to 5000 ppm, from 5 ppm to 4000 ppm, particularly preferably from 10 ppm to 2000 ppm, where the ppm refer to the total composition.

In the alternative preferred "ready-to-use formulations" embodiment of the compositions according to the invention already mentioned above, the siloxane is present preferably in an amount of from 0.1 to 1000 ppm, preferably from 1 to 500 ppm, particularly preferably from 2 to 200 ppm, where the ppm relate to the total composition.

The compositions according to the invention can advantageously be incorporated into detergents and cleaners and in particular into cosmetic formulations.

Consequently, the present invention further provides the use of the compositions according to the invention for producing formulations, in particular cosmetic formulations, and also the formulations, in particular cosmetic formulations, which comprise the compositions according to the invention.

Preferred formulations according to the invention comprise, in addition to the compositions according to the invention, at least one further surfactant, in which case, for example, anionic, nonionic, cationic and/or amphoteric surfactants can be used. From an applications point of view, preference is given to mixtures of anionic and nonionic surfactants. The total surfactant content of the aqueous formulation is preferably 5 to 60% by weight and particularly preferably 15 to 40% by weight, based on the total formulation.

The formulations according to the invention can further comprise at least one additional component selected from the group of
emollients,
emulsifiers,
thickeners/viscosity regulators/stabilizers,
UV light protection filters,
antioxidants,
hydrotropes (or polyols),
solids and fillers,
film formers,
pearlescence additives,
deodorant and antiperspirant active ingredients,
insect repellents,
self-tanning agents,
preservatives,
conditioners,
parfums,
dyes,
odor absorbers,
cosmetic active ingredients,
care additives,
superfatting agents,
solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts used of these components, reference is made expressly to the relevant handbooks known to the person skilled in the art, for example K. Schrader, "Grundlagen and Rezepturen der Kosmetika [Fundamentals and principles of cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The compositions according to the invention and the formulations according to the invention comprising the compositions according to the invention can advantageously be used for cleaning surfaces, e.g. for cleaning leather. For this form of the use according to the invention, the surface is preferably the surface of a living being, in particular a person, with such surfaces being particularly preferably selected from skin and hair.

The examples listed below describe the present invention by way of example, without any intention of restricting the invention, the scope of application of which is apparent from the entirety of the description and the claims, to the embodiments specified in the examples.

EXAMPLES

Example 1

Preparation of Rhamnolipids

A fermentation with a *Pseudomonas putida* strain pBBR1MCS2-Plac-rhlABC-T-Ptac-rhlC-T comprising the rhamnolipid biosynthesis genes RhlA, RhlB and RhlC, the preparation of which is described in US2014296168, was carried out. The preculture in a shake flask was carried out as described in WO2012013554A1. For the main culture, a mineral medium (M9) was likewise employed. The fermentation was conducted in a 2 litre fermenter in a carbon-limited manner via a glucose feed input. The glucose feed input takes place by reference to the dissolved oxygen signal. The dissolved oxygen was regulated at 20% saturation via the stirrer speed. The pH is regulated to 7 via a pH electrode and addition of 2M sulphuric acid or a 20% by weight ammonia solution. To prevent excessive foaming of the fermentation broth, the defoamer DOW Corning 1500 was added as required. The fermentation was conducted over 4 days to a dry biomass of 15 g/l. The rhamnolipid concentration was determined by HPLC and was 9.8 g/l. After separating off the cells by means of centrifugation at 10,000 g, the fermentation broth was adjusted to a pH of 3.1 by adding concentrated $H_2SO_4$. Renewed centrifugation at 500 g gave a pasty solid concentrate with a RL fraction of 45% by weight and with a viscosity of >10,000 mPas. With continuous stirring, a 50% strength by weight aqueous KOH solution was added to the pasty suspension of the concentrated rhamnolipid precipitate and a pH of 6 was established. The paste-like mass liquefied at this point with an accompanying sharp drop in viscosity. The suspension became a clear solution. By adding water, the solution was adjusted to an active content of 35% by weight. The rhamnolipid purity was >90% by weight, based on the dry mass.

Rhamnolipid species detected by means of HPLC were:

| RL total [%] (HPLC) | 91 |
| diRL-C8C10 | 13.9 |
| monoRL-C8C10 | 0.51 |
| diRL-C10C10 | 61.4 |
| monoRL -C10C10 | 1.4 |
| diRL-C10C12:1 | 5.9 |
| diRL-C10C12 | 5.5 |
| other RL | 2.2 |

Example 2

Preparation of Mono-rhamnolipids

The 35% by weight rhamnolipid solution prepared as described above was diluted to 1% by adding water. Two litres of this solution were heated to 50° C. With gentle stirring, 200 units of a thermostable rhamnosidase (ThermoActive™ Rhamnosidase A, Prokazyme) were added and the reaction was carried out overnight. After 20 h, a sample of the solution was analysed by means of HPLC. The di-rhamnolipid had been completely converted to mono-rhamnolipid and rhamnose. Then, the enzyme was deactivated for one hour at 80° C. The entire mixture was then freeze-dried. The freeze-dried product was adjusted to a mono-rhamnolipid active content of 35% by weight by adding water.

Example 3

Siloxanes Used

Siloxane 1, organomodified
$MD_{80}D^1{}_8M$
$R^{S2}=Me,$

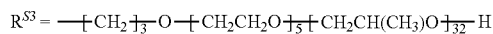

Siloxane 2 (silicone oil)
$MD_{78}M$
Siloxane 3, organomodified
$M^1D_{18}M^1$
$R^{S2}=Me,$

Siloxane 4, organomodified
$MD_{80}D^1{}_8M$
$R^{S2}=Me,$

Siloxane 5, organomodified
$M^1D_{18}M^1$
$R^{S2}=Me,$

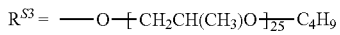

Siloxane 1, 3 and 4 are polyethersiloxanes in which the polyether radical is bonded to the siloxane backbone via an SiC group. These were prepared analogously to Example 1 in EP1520870.

Siloxane 5 is a polyethersiloxane in which the polyether radical is bonded to the siloxane backbone via an SiOC function. This compound was prepared as described in Comparative Example A 1.b from EP1627892

Siloxane 2 is a polydimethylsiloxane which was acquired from Gelest (Product Code: DMS-T21).

Furthermore, the following commercially available siloxanes were used:

Siloxane 6: Abil® T Quat 60 from Evonik Industries (INCI: Silicone Quaternium-22)

Siloxane 7: Dow Corning® 2-8566 Amino Fluid (INCI: Amodimethicone)

Siloxane 8: Dow Corning® BMW 2220 Non-ionic Emulsion (INCI: Divinyldimethicone/Dimethicone Copolymer and C12-13 Pareth-23 and C12-13 Pareth-3)

Siloxane 9: Dow Corning® Dimethiconol Blend 20 (INCI: Dow Corning, Dimethiconol and Dimethicone)

Siloxane 10: Abil® Soft AF 200 from Evonik Industries (INCI: Aminopropyl Dimethicone)

Siloxane 11: Abil® Wax 9840 from Evonik Industries (INCI: Cetyl Dimethicone)

Example 4

Preparation of the Rhamnolipid/siloxane Compositions

The siloxanes were added dropwise to the 35% by weight rhamnolipid solution (Example 1) with slow stirring on the magnetic stirrer at 50° C., and stirring was continued for one hour. The rhamnolipid content was adjusted to 30% by weight by subsequently adding water.

TABLE 1

Aqueous rhamnolipid composition (data in % by weight in water) with increasing fraction of siloxane

| | Composition | | | | | |
| --- | --- | --- | --- | --- | --- | --- |
| | 1a | 1b* | 1c* | 1d* | 1e* | 1f |
| RL/siloxane ratio | — | 3000:1 | 1000:1 | 500:1 | 250:1 | 50:1 |
| RL content | 30.0% | 30.0% | 30.0% | 30.0% | 30.0% | 30.0% |
| Siloxane 1 | | 0.01% | 0.03% | 0.06% | 0.12% | 0.6% |

*= according to the invention

TABLE 2

Aqueous rhamnolipid composition with different siloxanes (data in % by weight in water)

| | Composition | | | | | | |
|---|---|---|---|---|---|---|---|
| | 2a | 2b | 2c* | 2d | 2e* | 2f | 2g* |
| RL/siloxane ratio | — | 50:1 | 1000:1 | 50:1 | 1000:1 | 50:1 | 1000:1 |
| RL content | 30.0% | 30.0% | 30.0% | 30.0% | 30.0% | 30.0% | 30.0% |
| Siloxane 1 content | | 0.6% | 0.03% | | | | |
| Siloxane 2 content | | | | 0.6% | 0.03% | | |
| Siloxane 3 content | | | | | | 0.6% | 0.03% |

| | Composition | | | |
|---|---|---|---|---|
| | 2h | 2i* | 2j | 2k* |
| RL/siloxane ratio | 50:1 | 1000:1 | 50:1 | 1000:1 |
| RL content | 30.0% | 30.0% | 30.0% | 30.0% |
| Siloxane 4 content | 0.6% | 0.03% | | |
| Siloxane 5 content | | | 0.6% | 0.03% |

In order to prepare different ratios of di- to mono-rhamnolipid, the rhamnolipid solutions from Example 1 and Example 2 were mixed in different ratios. Then, as described above, siloxane was added and the total rhamnolipid contents was adjusted to 30% by weight by adding water.

TABLE 3

Aqueous rhamnolipid composition with siloxane and different mono-/di-rhamnolipid ratios (data in % by weight in water)

| | Composition | | | | | | | |
|---|---|---|---|---|---|---|---|---|
| | 3a | 3b* | 3c | 3d* | 3e | 3f* | 3g | 3h* |
| RL/siloxane ratio | 50:1 | 1000:1 | 50:1 | 1000:1 | 50:1 | 1000:1 | 50:1 | 1000:1 |
| di-Rhamnolipid pH = 6 | 22.5% | 22.5% | 15.0% | 15.0% | 7.5% | 22.5% | 0% | 0% |
| mono-Rhamnolipid pH 6 | 7.5% | 7.5% | 15.0% | 15.0% | 7.5% | 67.5% | 30.0% | 30.0% |
| Siloxane 1 | 0.6% | 0.03% | 0.6% | 0.03% | 0.6% | 0.03% | 0.6% | 0.03% |

TABLE 4

Aqueous rhamnolipid composition with further siloxanes (data in % by weight in water)

| | Composition | | | | | |
|---|---|---|---|---|---|---|
| | 4a* | 4b* | 4c* | 4d* | 4e* | 4f* |
| RL/Siloxane Ratio | 1000:1 | 1000:1 | 1000:1 | 1000:1 | 1000:1 | 1000:1 |
| RL Content | 30.0% | 30.0% | 30.0% | 30.0% | 30.0% | 30.0% |
| Siloxane 6 Content | 0.03% | | | | | |
| Siloxane 7 Content | | 0.03% | | | | |
| Siloxane 8 Content | | | 0.03% | | | |
| Siloxane 9 Content | | | | 0.03% | | |
| Siloxane 10 Content | | | | | 0.03% | |
| Siloxane 11 Content | | | | | | 0.03% |

TABLE 5

Aqueous rhamnolipid composition with different rhamnolipid/siloxane ratios and concentrations (data in % by weight in water)

| Composition | 5a* | 5b* | 5c* | 5d* |
|---|---|---|---|---|
| RL/Siloxane Ratio | 1000:1 | 1000:1 | 5000:1 | 10000:1 |
| RL Content | 30.0% | 15.0% | 30.0% | 60.0% |
| Siloxane 4 Content | 0.03% | 0.015% | 0.006% | 0.006% |

Example 5

Application Test Leather

Velour leather strips (15×5 cm) were covered with a fine test dust (KSL Staubtechnik GmbH) in accordance with DIN EN 60068-2-68. Then, as much as possible of the dust was removed from the leather strips by shaking. The compositions described in Tables 1, 4 and 5 were diluted to a rhamnolipid content of 10% by weight by adding water. The solutions were stirred on a magnetic stirrer and in each case one soiled velour leather strip was placed into one of the solutions for 20 seconds. Then, the velour leather strips were rinsed under running tap water for 20 seconds and then dried in a drying cabinet at 40° C. for 24 h. A group of 10 test persons assessed the retention of the velour leather structure compared to an untreated velour leather strip and the cleaning effect, i.e. the dust removal compared to a soiled, non-cleaned velour leather section.

TABLE 6

Results of the investigations relating to the cleaning of velour

| | Composition | | | | | |
|---|---|---|---|---|---|---|
| | 1a | 1b* | 1c* | 1d* | 1e* | 1f |
| Retention of the suede structure (1 = unchanged, 5 = greatly changed) | 2.4 | 1.5 | 1.3 | 1.6 | 2.0 | 3.2 |
| Dust removal (1 = complete, 5 = no cleaning effect) | 3.3 | 2.6 | 2.1 | 2.0 | 2.2 | 2.5 |

| | Composition | | | | | |
|---|---|---|---|---|---|---|
| | 4a* | 4b* | 4c* | 4d* | 4e* | 4f* |
| Retention of the suede structure (1 = unchanged, 5 = greatly changed) | 1.4 | 1.5 | 1.7 | 1.6 | 1.8 | 1.5 |
| Dust removal (1 = complete, 5 = no cleaning effect) | 2.2 | 2.1 | 2.4 | 2.7 | 2.5 | 2.4 |

| | Composition | | | |
|---|---|---|---|---|
| | 5a* | 5b* | 5c* | 5d* |
| Retention of the suede structure (1 = unchanged, 5 = greatly changed) | 1.7 | 1.5 | 1.9 | 2.1 |
| Dust removal (1 = complete, 5 = no cleaning effect) | 2.3 | 2.2 | 2.6 | 2.8 |

Example 6

Application Test Odor Reduction and Skin Feel

To assess the odor reduction on the skin after cleaning with aqueous, surface-active formulations comprising rhamnolipid with different fractions of siloxane components, odor tests, which are described hereinbelow, were carried out by a trained odor panel (comprising at least 10 test persons).

50 g of cubed common onion were homogenized using a masher on level 2 for 2 minutes and the resulting paste was topped up to 1000 ml with a 0.5% strength solution of Tego Betain F 50 (Evonik Industries AG) in completely demineralized water. The suspension was then stirred with the help of a magnetic stirrer for 30 minutes at 680 rpm and at 25° C. using a stirring core (60 mm in length, 10 mm in diameter) in a 2l beaker (flat shape) covered with a watch glass and then filtered over a 190 μm Schnellsieb from Erich Drehkopf GmbH. In each case 2 ml of the resulting aqueous onion solution were applied using a pipette to the insides of the hands and spread on the palm with 10 uniform rubbing movements. The hands were then left to dry for 60 seconds at room temperature and an atmospheric humidity of (50+/−10)%. For this, the group of at least 10 trained test persons washed their hands in accordance with a precisely defined procedure using the compositions described in Table 2 and Table 3 and assessed the odor of the inside of the hands directly after handwashing and after 5 minutes using a grading scale from 0 (no odor detectable) to 3 (very strong odor, very unpleasant). Additionally, the skin feel was assessed by reference to a grading scale from 1 (very good) to 5 (very poor). To assess the odor reduction of product examples according to the invention, odor panel tests were also carried out compared to the secondary surfactant cocamidopropyl betaines, which is widespread in the industry as a universal surfactant.

TABLE 7

Result of handwashing test

| | Composition | | | | | | |
|---|---|---|---|---|---|---|---|
| | Cocamidopropyl Betaine (30%) | 2a | 2b | 2c* | 2e* | 2g* | 2i* |
| Odor (0 = no odor detectable to 3 = very strong odor, very unpleasant) | 2.7 | 2.3 | 2.4 | 1.2 | 1.2 | 0.7 | 1.5 |
| Skin feel during washing (1 = very good, 5 = very poor) | 2.7 | 2.3 | 1.6 | 1.7 | 2.0 | 1.8 | 2.1 |

| | Composition | | | | |
|---|---|---|---|---|---|
| | 2k* | 3b* | 3d* | 3f* | 3h* |
| Odor (0 = no odor detectable to 3 = very strong odor, very unpleasant) | 1.4 | 0.9 | 1.1 | 1.3 | 1.2 |
| Skin feel during washing (1 = very good, 5 = very poor) | 2.0 | 2.3 | 1.9 | 2.1 | 1.7 |

It is evident from the measurement results that the handwashing with the formulations according to the invention using the compositions according to the invention brings about the greatest odor reduction, with a good skin feel being present.

Formulation Examples

"Compositions" are those in Tables 1 to 3 above

Lauryl Ether Sulphate-based Systems:

Moisturizing Skin Cleanser

| | | |
|---|---|---|
| A | Sodium Laureth Sulfate | 8.0% |
| | Composition 1e* | 2.0% |
| | Parfum | q.s. |
| B | Water | to 100% |
| | Hydroxypropyl Methyl Cellulose | 1.2% |
| | Cocamidopropyl Betaine | 3.0% |
| | PPG-3 Myristyl Ether | 1.0% |
| | Glycol Distearate | 2.0% |
| | PEG-200 Hydrogenated Glyceryl Palmate (and) PEG-7 Glyceryl Cocoate | 1.0% |
| | Preservative | q.s. |
| | Citric Acid, 30% | to pH 5.5 |

Body Cleanser with Pearl Effect

| | |
|---|---|
| Sodium Laureth Sulfate | 9.0% |
| Composition 1d* | 2.5% |
| Water | to 100% |
| Cocamidopropyl Betaine | 1.5% |
| Glycol Distearate (and) Laureth-4 (and) Cocamidopropyl Betaine | 2.0% |
| PEG-18 Glyceryl Oleate/Cocoate | 1.5% |
| NaCl | 0.5% |
| Parfum | q.s. |
| Preservative | q.s. |

Hand Cleaning Paste

| | |
|---|---|
| Water | to 100% |
| Laureth-5 | 5.0% |
| *Juglans Regia* | 3.0% |
| Sodium Laureth Sulfate | 5.0% |
| Composition 2c* | 2.0% |
| Bentonite | 1.0% |
| Sodium Cocoamphoacetate | 0.7% |
| Oleic Acid | 0.5% |
| C12-13 Alkyl Lactate | 0.5% |
| *Aloe Barbadensis* | 0.3% |
| Sodium Chloride | 0.3% |
| PEG-14M | 0.2% |
| Citric Acid | to pH 6.0 |
| Preservative, Parfum | q.s. |

Skin Cleanser

| | |
|---|---|
| Water | to 100% |
| Ammonium Laureth Sulfate | 5.5% |
| Cocamidopropyl Betaine | 2.5% |
| Composition 2e* | 1.5% |
| Sorbitol | 1.2% |
| Cocamide Methyl MEA | 0.7% |
| PEG-7 Glyceryl Cocoate | 0.6% |
| Sodium Cocoyl Alaninate | 0.8% |
| Sodium Chloride | 0.7% |
| DMDM Hydantoin | 0.1% |
| Disodium EDTA | 0.1% |
| *Santalum Album* Extract (Extract) | 0.1% |
| Lactic Acid, 90% | to pH 5.5 |
| Preservative, Parfum | q.s. |

Alkyl Sulfate-based Systems:
Care Body Cleanser

| | |
|---|---|
| Water | to 100% |
| Ammonium Lauryl Sulfate | 5.0% |
| Lauryl Glucoside | 3.0% |
| Cocamidopropyl Betaine | 2.5% |
| Composition 3b* | 2.0% |
| Lauroyl Sarcosine | 0.7% |
| *Bambusa Arundinacea* Extract | 1.0% |
| *Citrus Grandis* Extract | 1.0% |
| Alcohol | 0.7% |
| Hydroxypropyl Guar Hydroxypropyltrimonium Chloride | 0.3% |
| *Citrus Medica* Limonum Oil | 0.3% |
| Preservative, Parfum | q.s. |

Mild Washing Lotion

| | |
|---|---|
| Water | to 100% |
| Sodium Coco Sulfate | 5.5% |
| Glycerin | 3.5% |
| Composition 3d* | 3.0% |
| Decyl Glucoside | 1.5% |
| Alcohol | 1.0% |
| Xanthan Gum | 1.0% |
| *Bellis Perennis* Extract | 0.7% |
| *Arnica Montana* Extract | 0.7% |
| *Chamomilla Recutita* Extract | 0.5% |
| Disodium Cocoyl Glutamate | 0.5% |
| Sodium Cocoyl Glutamate | 0.3% |
| Preservative, Parfum | q.s. |

Betaine-based Systems:
Mild, Sulfate-free Body Cleanser

| | |
|---|---|
| Cocamidopropyl Betaine | 5.0% |
| Sodium Cocoamphoacetate | 4.0% |
| Composition 3f* | 1.5% |
| Sucrose Cocoate | 1.5% |
| PEG-120 Methyl Glucose Dioleate | 2.0% |
| Polyquaternium-10 | 0.2% |
| Water | to 100% |
| Citric Acid, 30% | to pH 6.0 |
| Preservative, Parfum, Dyes | q.s. |

Mild, PEG-free Body Cleanser

| | |
|---|---|
| Water | to 100% |
| Cocamidopropyl Betaine | 5.5% |
| Lauryl Glucoside | 3.0% |
| Sodium Cocoamphoacetate | 3.0% |
| Composition 1c* | 3.0% |
| Hydroxypropyl Methyl Cellulose | 0.5% |
| Isostearamide MIPA (and) Glyceryl Laurate | 1.4% |
| Polyquaternium-7 | 0.5% |
| Citric Acid, 30% | to pH 5.0 |
| Parfum, Preservative | q.s. |

Amphoacetate-based Systems:
Body Cleanser, PEG- & Sulfate-free

| | |
|---|---|
| Water | to 100% |
| Sodium Cocoamphoacetate | 5.0% |
| Disodium Lauryl Sulfosuccinate | 1.2% |
| Composition 1c* | 2.5% |
| Cocamidopropyl Betaine | 3.0% |
| Cocamidopropyl Betaine (and) Glyceryl Laurate | 1.0% |
| Citric Acid, 30% | to pH 5.0 |
| Preservative, Parfum | q.s. |

Shampoo, PEG- & Sulfate-free

| | |
|---|---|
| Water | to 100% |
| Sodium Cocoamphoacetate | 5.5% |
| Disodium Cocoyl Glutamate | 2.0% |
| Composition 2g* | 2.0% |
| Polyquaternium-10 | 0.2% |
| Palmitamidopropyltrimonium Chloride | 1.0% |
| Isostearamide MIPA | 1.0% |
| Citric Acid, 30% | to pH 5.5 |
| Preservative, Parfum | q.s. |

APG-based Systems:
Mild Body Cleanser

| | |
|---|---|
| Water | to 100% |
| Lauryl Glucoside | 5.0% |
| Coco Glucoside | 2.0% |
| Composition 2i* | 3.0% |
| Sucrose Cocoate | 1.5% |
| Cocamidopropyl Betaine | 4.0% |

| | |
|---|---|
| Carbomer | 1.0% |
| Citric Acid, 30% | to pH 5.5 |
| Preservative, Parfum | q.s. |

Shower Gel

| | |
|---|---|
| Water | to 100% |
| Composition 2k* | 4.0% |
| Coco Glucoside | 4.0% |
| Glycerin | 3.0% |
| Disodium Cocoyl Glutamate | 2.0% |
| Sodium Cocoyl Glutamate | 2.0% |
| Polyglyceryl-10 Laurate | 1.0% |
| Glyceryl Caprylate | 1.0% |
| *Rubus Idaeus* (Raspberry) Fruit Extract | 0.3% |
| Sodium PCA | 0.2% |
| Xanthan Gum | 0.6% |
| Glyceryl Oleate | 0.3% |
| Phytic Acid | 0.1% |
| Citric Acid | to pH 5.5 |
| Parfum | q.s. |

Mild Hair & Body Cleanser, ECOCERT Ingredients

| | |
|---|---|
| Lauryl Glucoside | 3.0% |
| Composition 1c* | 2.0% |
| Cocamidopropyl Betaine (and) Glyceryl Laurate | 5.0% |
| Sorbitan Sesquicaprylate | 0.9% |
| Water | to 100% |
| Cocamidopropyl Betaine | 4.0% |
| Citric Acid, 30% | to pH 5.5 |
| Preservative, Parfum | q.s. |

Mild Cleansing Foam

| | |
|---|---|
| Water | to 100% |
| Glycine Soya Oil | 8.0% |
| Glycerin | 5.0% |
| Alcohol | 5.0% |
| Composition 3h* | 4.0% |
| Coco Glucoside | 3.5% |
| Caprylic/Capric Triglyceride | 2.0% |
| Sodium Coco Sulfate | 2.0% |
| Sodium Lactate | 1.0% |
| Sodium Cocoyl Glutamate | 1.0% |
| Disodium Cocoyl Glutamate | 0.6% |
| *Argania Spinosa* Kernel Oil | 0.6% |
| Preservative, Parfum | q.s. |

Mild Body Cleanser, PEG- and Sulphate-free

| | |
|---|---|
| Lauryl Glucoside | 3.5% |
| Composition 3h* | 2.0% |
| Isostearamide MIPA (and) Glyceryl Laurate | 1.0% |
| Water | to 100% |
| Coco Glucoside | 1.0% |
| Sodium Cocoamphoacetate | 3.0% |
| Cocoamidopropyl Betaine | 3.5% |
| Citric Acid, 30% | to pH 5.5 |
| Preservative, Parfum | q.s. |

Sulfonate-based System:
Sulfate-free Body Cleanser

| | |
|---|---|
| Water | to 100% |
| Sodium C14-16 Olefin Sulfonate | 4.0% |
| Composition 1c* | 3.0% |
| Cocoamidopropyl Betaine | 3.0% |
| Methylhydroxyethylcellulose | 1.5% |
| Preservative, Parfum | q.s. |

Sulfosuccinate-based Systems:
Mild Skin Cleanser

| | |
|---|---|
| Water | to 100% |
| Disodium Laureth Sulfosuccinate | 3.5% |
| Composition 1c* | 3.5% |
| Isostearamide MIPA (and) Glyceryl Laurate | 1.7% |
| PEG-7 Glyceryl Cocoate | 0.5% |
| Sodium Cocoamphoacetate | 3.0% |
| Palmitamidopropyltrimonium Chloride | 2.3% |
| Citric Acid, 30% | to pH 6.0 |
| Preservative, parfum, dyes | q.s. |

Mild Skin Cleansing Foam

| | |
|---|---|
| Water | to 100% |
| Disodium PEG-5 Laurylcitrate Sulfosuccinate (and) Capryl/Capramidopropyl Betaine | 5.5% |
| Composition 1e* | 3.0% |
| Capryl/Capramidopropyl Betaine | 2.0% |
| Polyglyceryl-3 Caprate | 0.5% |
| Creatine | 0.2% |
| Hydroxypropyl Methyl Cellulose | 0.5% |
| Sodium Lactate (and) Sodium PCA (and) Glycine (and) Fructose (and) Urea (and) Niacinamide (and) Inositol (and) Sodium Benzoate (and) Lactic Acid | 1.0% |
| Preservative, Parfum | q.s. |

Sarcosinate-based Systems:
Skin Cleanser

| | |
|---|---|
| Water | to 100% |
| Sodium Lauroyl Sarcosinate | 5.0% |
| Coco Betaine | 3.0% |
| Composition 1e* | 3.0% |
| Cocamide DEA | 4.5% |
| Cetrimonium Chloride | 0.3% |
| Steralkonium Chloride | 0.1% |
| Disodium EDTA | 0.2% |
| Citric Acid | to pH 6.7 |
| Preservative, Parfum | q.s. |

Skin cleanser

| | |
|---|---|
| Water | to 100% |
| Sodium Lauroyl Sarcosinate | 5.0% |
| Composition 1c* | 2.5% |
| Cocamidopropyl Betaine | 4.0% |
| Palmitamidopropyltrimonium Chloride | 0.5% |
| Polyquaternium-10 | 0.1% |
| Citric Acid | to pH 5.1 |
| Preservative, Parfum | q.s. |

Other-based Systems (Sultain, Anisate, Isethionate, Glutamate, Glycinate):
Shower Gel

| | |
|---|---|
| Water | to 100% |
| Sodium Lauroyl Methyl Isethionate | 4.5% |
| Composition 1c* | 3.0% |
| Cocamidopropyl Betaine | 2.5% |
| Sodium Chloride | 2.5% |

-continued

| | |
|---|---|
| Glycerin | 1.5% |
| Polyglyceryl-4 Caprate | 0.6% |
| Sucrose Cocoate | 0.5% |
| Trisodium Ethylenediamine Disuccinate | 0.2% |
| Zinc Laurate | 0.1% |
| Salicylic Acid | 0.1% |
| Propylene Glycol | 0.1% |
| *Aloe Barbadensis* Leaf Juice | 0.1% |
| Sodium Hydroxide | 0.1% |
| Tocopherol | 0.1% |
| Citric Acid | to pH 5.5 |
| Preservative, Parfum | q.s. |

Foaming Body Cleanser

| | |
|---|---|
| Water | to 100% |
| Sodium Cocoyl Glycinate | 6.0% |
| Composition 1e* | 4.0% |
| Coco-betaine | 2.0% |
| Glycerin | 1.0% |
| Sodium Chloride | 1.0% |
| Acrylates/C10-30 Alkyl Acrylate Crosspolymer | 0.5% |
| Sodium Hydroxide | 0.4% |
| PEG-14M | 0.3% |
| Salicylic Acid | 0.1% |
| Polyquaternium-10 | 0.1% |
| Glycol Distearate | 0.2% |
| Citric Acid | to pH 5.5 |
| Preservative, Parfum, Dyes | q.s. |

The invention claimed is:

1. An aqueous skin cleansing composition comprising a rhamnolipid and a siloxane,
   wherein the rhamnolipid comprises a rhamnolipid salt comprising rhamnolipid anions and cations selected from the group consisting of $Li^+$, $Na^+$, $K^+$, $Mg^{2+}$, $Ca^{2+}$, $Al^{3+}$, $NH_4^+$, and triethanolammonium,
   wherein the weight ratio of the rhamnolipid to the siloxane is from 25,000:1 to 2,500:1,
   wherein the weight ratio of the rhamnolipid to the siloxane is the sum of all the rhamnolipid contained in the composition to the siloxane of all siloxanes contained in the composition,
   wherein the composition comprises a mixture of rhamnolipid,
   wherein the weight ratio of di-rhamnolipids to mono-rhamnolipids in the mixture is greater than 98:2,
   wherein the composition comprises rhamnolipid in an amount of from 12% by weight to 70% by weight, wherein the percentages by weight refer to the total composition and take all rhamnolipid present in the composition, and
   wherein the rhamnolipid mixture comprises
      from 51% by weight to 95% by weight of diRL-C10C10, and
      from 0.5% by weight to 9% by weight of monoRL-C10C10,
      where the percentages by weight refer to the sum total of all rhamnolipids present.
2. The aqueous skin cleansing composition according to claim 1, wherein the composition comprises the rhamnolipid in an amount of from 15% by weight to 60% by weight, wherein the percentages by weight refer to the total composition, and
   wherein the rhamnolipid mixture comprises
      from 70% by weight to 90% by weight of diRL-C10C10,
      from 0.5% by weight to 3% by weight of monoRL-C10C10, and
      from 0.5% by weight to 15% by weight of diRL-C10C12:1,
      where the percentages by weight refer to the sum total of all rhamnolipids present.
3. The aqueous skin cleansing composition according to claim 1, wherein the composition comprises the rhamnolipid in an amount of from 25% by weight to 50% by weight wherein the percentages by weight refer to the total composition.
4. The aqueous skin cleansing composition according to claim 1, wherein the composition comprises a mixture of rhamnolipid, where the weight ratio of di-rhamnolipids to mono-rhamnolipids in the mixture is greater than 51:49.
5. The aqueous skin cleansing composition according to claim 1, wherein the composition is an aqueous composition and has a pH of from 5.5 to 6.9.
6. The aqueous skin cleansing composition according to claim 1, wherein the composition comprises of rhamnolipid anions in an amount of from 70% by weight to 95% by weight wherein the percentages by weight refer to the total composition.
7. The aqueous skin cleansing composition according to claim 1, wherein the siloxane is selected from the group consisting of silicone oils, silicone waxes, silicon-functional siloxanes, organofunctional siloxanes, polydiethylsiloxanes, siloxanes having functional groups and organomodified siloxanes.
8. The aqueous skin cleansing composition according to claim 1, wherein the siloxane is present in an amount of from 0.1 ppm to 5000 ppm by weight of the composition.
9. A formulation comprising the aqueous skin cleansing composition according to claim 1.
10. The formulation according to claim 9, wherein the formulation comprises at least one further surfactant.
11. A cleaning surface comprising the aqueous skin cleansing composition according to claim 1.
12. The aqueous skin cleansing composition according to claim 1, wherein the rhamnolipid mixture comprises
      from 75% by weight to 85% by weight of diRL-C10C10,
      from 0.5% by weight to 2% by weight of monoRL-C10C10,
      from 0.5% by weight to 15% by weight of diRL-C10C12:1,
      where the percentages by weight refer to the sum total of all rhamnolipids present.
13. The aqueous skin cleansing composition according to claim 1, wherein the rhamnolipid mixture comprises
      from 0.5% by weight to 3% by weight of monoRL-C10C12, and
      from 0.1% by weight to 5% by weight of monoRL-C10C12:1,
      where the percentages by weight refer to the sum total of all rhamnolipids present.
14. The aqueous skin cleansing composition according to claim 1, wherein the composition comprises the rhamnolipid in an amount of from 2% by weight to 60% by weight, where the percentages by weight refer to the total composition.
15. The aqueous skin cleansing composition according to claim 1, wherein the composition comprises the rhamnolipid in an amount of from 20% by weight to 50% by weight, where the percentages by weight refer to the total composition.
16. The composition according to claim 1, wherein the rhamnolipid mixture comprises
      from 0.5% by weight to 2% by weight of monoRL-C10C12, and
      from 0.5% by weight to 3% by weight of monoRL-C10C12:1,
      where the percentages by weight refer to the sum total of all rhamnolipids present.
17. The aqueous skin cleansing composition according to claim 1, wherein the composition is an aqueous composition and has a pH of from 5.6 to 6.0.

18. The aqueous skin cleansing composition according to claim 1, wherein the composition comprises rhamnolipid cations in an amount of from 80% by weight to 90% by weight of all cations present in the composition except $H^+$ and $H_3O^+$.

19. The aqueous skin cleansing composition according to claim 1, wherein the siloxane is selected from polyethersiloxanes of formula II:

$$M_a M^1_b D_c D^1_d T_e Q_f \qquad \text{Formula II}$$

wherein

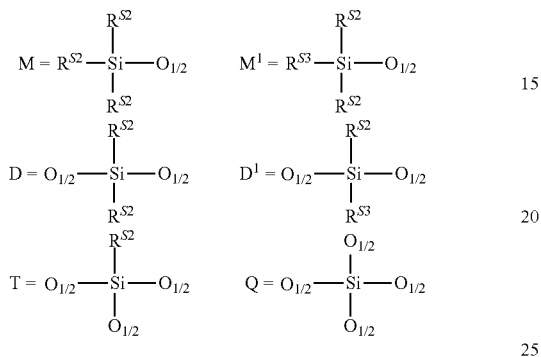

a = 2-10,
b = 0-10,
c = 3-500,
d = 1.5-15,
e = 0-10,
f = 0-10,
wherein, a+b≥2 and N=a+b+c+d+e+f≤2050, and b+d≥1
$R^{S2}$ is selected from the group consisting of alkyl radicals having 1-16 carbon atoms, aryl radicals having 6-16 carbon atoms, H, and $OR^{S4}$,
$R^{S4}$ is selected from the group consisting of alkyl radicals having 1-16 carbon atoms, aryl radicals having 6-16 carbon atoms, and H,
$R^{S3}$ is selected from the group consisting of polyether radicals, of the general formula III

Formula III wherein
$R^{S5}$ is selected from the group consisting of alkyl radicals having 1 to 18 carbon atoms which have ether functions, or aryl radicals having 6-18 carbon atoms,
$R^{S6}$ is selected from the group consisting of $R^{S8}$, H, —C(O)$R^{S8}$,
$R^{S7}$ is selected from the group consisting of divalent organic radicals,
$R^{S8}$ is selected from the group consisting of alkyl radicals having 1-16 carbon atoms and aryl radicals having 6-16 carbon atoms, wherein
h=0 or 1,
i=0-50,
j=0-50,
k=0-50,
l=0-40,
wherein i+j+k+l≥3.

20. The aqueous skin cleansing composition according to claim 1, wherein the siloxane is present in an amount of from 1 ppm to 500 ppm by weight of the composition.

* * * * *